United States Patent [19]

Tisserat

[11] Patent Number: 5,196,336

[45] Date of Patent: Mar. 23, 1993

[54] ADVENTITIOUS CITRUS JUICE VESICLES FROM PRE-EXISTING JUICE VESICLES

[75] Inventor: Brent Tisserat, Upland, Calif.

[73] Assignee: The United States of America as represented by the Secretary of Agriculture, Washington, D.C.

[21] Appl. No.: 389,194

[22] Filed: Aug. 3, 1989

[51] Int. Cl.$^5$ .............................................. A01H 5/08
[52] U.S. Cl. .......................... 435/240.4; 435/240.45; 800/200; 800/DIG. 38; 800/DIG. 39
[58] Field of Search ........... 435/240.4, 240.45, 240.51; 800/200, DIG. 38, DIG. 39

[56] References Cited

PUBLICATIONS

Tisserat, et al. (Feb. 28, 1989) Amer. J. Bot. 76:238-246.
Altman et al. (1982) Plant Physiol 69:1-6.
Tisserat et al. (Feb. 1989) Food Technology 43:95-100.
H. A. Kordan, "Proliferation of Excised Juice Vesicles of Lemon in Vitro," *Science* 129: 779-780 (1959).
T. Murashige and D. P. H. Tucker, "Growth Factor Requirements of Citrus Tissue Culture," *Proceedings First International Citrus Symposium* 3: 1155-1161 (1969).
J. W. Einset, "Citrus Tissue Culture, Stimulation of Fruit Explant Cultures With Orange Juice," *Plant Physiology* 62: 885-888 (1978).
J. W. Unger and K. A. Feng, "Growth and Differentiation of Juice Vesicles of Orange Grown In Vitro," *American Journal of Botany* 65: 511-515 (1978).
Y. Kato, "Studies on Juice Vesicles Isolated from Mature and Immature Citrus Fruit," *J. Japan. Soc. Hort. Sci.* 49: 36-40 (1980).
A. Altman, Y. Gülsen, and R. Goren, "Growth and Metabolic Activity of Lemon Juice Vesicles Explants in Vitro," *Plant Physiology* 69: 1-6 (1982).
B. Tisserat and P. D. Galletta, "In Vitro Culture of Lemon Juice Vesicles," *Plant Cell, Tissue, and Organ Culture* 11: 81-95 (1987).
Y. Gülsen, A. Altman, and R. Goren, "Growth and Development of Citrus pistils and Fruit Explants In Vitro," *Physiol Plant* 53: 295-300 (1981).

*Primary Examiner*—Che S. Chereskin
*Attorney, Agent, or Firm*—M. Howard Silverstein; John D. Fado; Margaret A. Connor

[57] ABSTRACT

Novel adventitious citrus juice vesicles which have the unique characteristic that they branch out of pre-existing citrus juice vesicles are disclosed. The citrus vesicles are prepared by culturing juice vesicles obtained from fruit 120-210 days old on a medium comprising a growth regulator, sugar, inorganic salts, and vitamins. The product is useful as edible citrus tissue or for citrus juice.

5 Claims, No Drawings

ADVENTITIOUS CITRUS JUICE VESICLES FROM PRE-EXISTING JUICE VESICLES

BACKGROUND OF THE INVENTION

1. Field of the Invention

The present invention relates to adventitious citrus juice vesicles having the unique characteristic that they branch out of pre-existing citrus juice vesicles cultured in vitro.

2. Description of the Art

The citrus fruit is unique among the angiosperms. The fruit is a berry (hesperidium) consisting of 6-20 united carpels. These carpels are oriented vertically with their margins curved adaxially to join the floral axis thus forming locules. Exterior to the locules is the pericarp which is subdivided into three regions. The exocarp or flavedo (exterior peel) consists of the outermost layers of the fruit. The endocarp is the inner portion of the pericarp and a portion of the locular membrane. The mesocarp or albedo occurs between the exocarp and endocarp (H. Schneider, Chapter 1, "The Anatomy of Citrus," in *The Citrus Industry*, Vol. II, Eds. W. Reuther et al., University of California Press, pp. 1-85, 1968).

Citrus juice vesicles are an organized, specialized group of cells which accumulate juice. In nature, they arise from primordial bumps on the surface of the citrus endocarp and grow from the endocarp into the locules where they compactly fill the locules. Through cell division they differentiate into elliptical-shaped juice vesicles consisting of a distinct stalk and a single terminal body with tapered ends. They are characterized as being uniform solitary stalked structures. The mature vesicles are saclike in nature; the exterior skin encloses large vacuolated cells containing the materials which make up the juice. Juice vesicle cells are unique in terms of fruit anatomy. In these cells, the vacuole is very large, almost completely filling the interior of the cell.

Citrus juice vesicles make up the edible portion of the citrus fruit, and therefore they are of great economic value. The conventional method of producing edible citrus tissue, i.e., juice vesicles, has been to establish citrus trees in soil, cultivate them for years and then once they fruit, harvest the citrus fruit. The edible endocarp tissue is consumed either as fresh fruit or is processed to produce citrus juice. This method of producing fruit and endocarp tissue has several drawbacks. It requires much land for citrus fruit cultivation and is very labor intensive. Further, in usual husbandry practices, the fruit is periodically exposed pesticides and herbicides which have the potential for harm to man, beneficial insects, and the environment.

Various investigators have reported research on in vitro culture of citrus vesicles or explants. Production of new juice vesicles was not found. Rather, the primary result was the deterioration of tissue into a callus mass. Y. Gulsen et al., *Physiologia Plantarum* 53: 295-300 (1981) reported the formation in culture of atypical juice vesicles from the inner part of the explant (normal vesicle formation) and were normally situated on a stalk which arose from a cushion of callus.

SUMMARY OF THE INVENTION

The invention comprises adventitious citrus juice vesicles having the unique characteristic that they branch out of pre-existing citrus juice vesicles. This is in contrast to tree-produced citrus juice vesicles which arise from the endocarp of the citrus fruit.

The adventitious citrus juice vesicles optionally have the additional characteristics: they have the ability to produce additional adventitious citrus juice vesicles through branching and they are generally elliptical in shape.

To obtain the novel juice vesicles, citrus juice vesicles from immature citrus fruit are cultured on a medium comprising an effective amount of a growth regulator, sugar, inorganic salts, and vitamins. An important feature is that only minimal callusing occurs.

Advantages of the adventitious juice vesicles of the invention over conventional tree-produced citrus juice vesicles include the following: (1) vast quantities of valuable agricultural land are not required for production because the adventitious juice vesicles are produced in a culture environment, (2) spraying with pesticides and herbicides is not required because the adventitious vesicles are grown in a sterile environment, (3) influence of the weather and adverse physical environments is eliminated since vesicles are grown in a controlled environment, (4) requirement for shipping is minimized since vesicles could be grown next to processing plants, and (5) crop production yields could be predictable and increased by growing vesicles in a laboratory versus the growing of fruit on trees in fields subject to varying weather conditions, pests, and the like.

In accordance with this discovery it is an object of the invention to provide adventitious citrus juice vesicles that is, juice vesicles having the unique property that they branch out of pre-existing juice vesicles.

Another object of the invention is the utilization of juice vesicle explants for the production of citrus fruit tissue.

A further object of the invention is to eliminate the disadvantages associated with producing edible citrus fruit tissue by cultivation of citrus fruit trees.

Other objects and advantages of the invention will become readily apparent from the ensuing description.

DETAILED DESCRIPTION OF THE INVENTION

The invention, for the first time, provides citrus juice vesicles from pre-existing juice vesicles. Because the new citrus juice vesicles are formed from an "unusual" place, that is, they are caused to initiate and grow out of (i.e., branch out of) pre-existing juice vesicles, rather than out of the endocarp which is where juice vesicles normally are formed, the new vesicles are denoted as "adventitious juice vesicles" or the equivalent expression "adventitious juice vesicle branches". Most commonly, the adventitious vesicles branch out of the growing tip region of the cultured vesicle; however, they may initiate anywhere on the surface of the cultured vesicle.

The term "citrus fruit" as used herein means fruit from trees or shrubs of the genus Citrus. This includes, for example, lemon, lime, orange (e.g., mandarin, navel, sour), grapefruit, pummelo, and tangelo.

To obtain adventitious citrus juice vesicles, juice vesicles from citrus fruit of a particular juvenile growth stage are cultured in vitro on a growth media containing a growth regulator, sugar, inorganic salts, and vitamins in an effective concentration, that is, in a concentration which causes the initiation and growth of adventitious juice vesicles as described in detail below. The juice vesicles used for in vitro production of adventitious juice vesicles must be from fruit at least 120 days old (counting from visible flower appearance). Production of adventitious juice vesicles from fruit less than 120 days is essentially negligible. Conversely, the fruit must not be mature. The upper age limit of the fruit is 210 days, and preferably 180 days.

An exemplary method to obtain the adventitious citrus juice vesicles of the invention is as follows. Citrus fruit having an age in the 120-210 day range are surface sterilized by any technique known in the art, for example, by treatment with 2.63% sodium hypochlorite solution for 30 minutes.

The sterilized fruit are sectioned into convenient size sections, e.g., halves, quarters, or isolated sections. One convenient procedure is to bisect the fruit equitorially or longitudinally and plant in the nutrient medium. Where isolated sections are used, a convenient size is 1 cm$^2$. In all cases, explants are obtained which have intact juice vesicles.

The explants are then transferred to a nutrient medium which contains a plant growth regulator, sugar, inorganic salts, and vitamins. As used herein, plant growth regulator is defined to mean any natural or synthetic compound which has a regulatory effect on plants or plant tissues. Plant growth regulators useful for this invention include, for example, (1) a gibberellic acid compound such as GA$_3$ or GA$_3$ methyl esters; (2) an auxin such as 2,4-dichlorophenoxyacetic acid (2,4-D); p-chlorophenoxyacetic acid; naphthaleneacetic acid (NAA); indoleacetic acid (IAA), or indole-3-butyric acid (IBA); and (3) 4-amino-3,5,6-trichloropyridine-2-carboxylic acid (picloram). Combinations of the aforementioned plant growth regulators may be used in the medium. Benzyladenine, used alone, is not suitable as the plant growth regulator to obtain adventitious citrus juice vesicles, but may be used in combination with the aforementioned plant growth regulators.

The plant growth regulator is present in the medium in an effective amount, that is, in an amount sufficient to initiate production of adventitious citrus juice vesicles (juice vesicle branches) from pre-existing juice vesicles cultured in vitro. Generally, 0.0001 to 300 mg and preferably 0.1 to 100 mg of plant growth regulator per liter of medium is utilized.

The medium contains sugar as a carbohydrate source. As used herein, sugar includes mono and disaccharides such as sucrose, glucose, fructose, galactose, maltose, and arabinose. Generally, 10000 to 75000, preferably about 30000 mg of sugar per liter of medium is used.

The inorganic salts comprise macroelements and microelements necessary for initiation and growth of adventitious citrus juice vesicles from pre-existing vesicles cultured in vitro. Exemplary media formulations of inorganic salts are shown in Tables 1-4. Optimum medium for a particular circumstance can be determined by routine experimentation.

The medium further contains vitamins as necessary for initiation and growth of adventitious citrus juice vesicles in vitro. Exemplary vitamins (and concentration ranges) are thiamine.HCl (0.030 to 0.5 mg/l) and inositol (50 to 150 mg/l).

A gelling agent such as agar is preferably added to the medium, at a concentration of 0.6 to 1%.

The medium is adjusted to a pH suitable for culturing citrus juice vesicles, generally in a range of about 5 to 6, preferably 5.7, and is sterilized by autoclaving.

The explants are planted in the medium and cultured. Exemplary culture conditions are 26° C. with a photoperiod of 16 hours.

The juice vesicle explants are cultured on the medium to initiate growth of adventitious citrus juice vesicle branches. Highly organized meristematic bodies that are identified as newly forming juice vesicle branches are initiated from the surface of the pre-existing juice vesicles in the culture medium. The explants are then preferably cultured to develop into mature juice vesicles. The developed adventitious vesicles have the property that they resemble normal citrus juice vesicles in that they are generally elliptical in shape.

In an alternate procedure to obtain adventitious citrus juice vesicles, the explant is cultured on the above medium for a time sufficient to initiate the production of adventitious juice vesicles branches and is then transferred to a nutrient medium having the constituents as described above with the exception that the second medium is devoid of a plant growth regulator. The latter medium is not useful for ready initiation of adventitious juice vesicles, but can be used to support growth of previously initiated adventitious juice vesicles.

TABLE 1 mg/l: KNO$_3$, 500; Ca(NO$_3$)$_2$.3H$_2$O, 500; MgSO$_4$.7H$_2$O, 150; MnSO$_4$.H$_2$O, 5; CuSO$_4$.5H$_2$O, 1; ZnSO$_4$.7H$_2$O, 2; MgCl$_2$.6H$_2$O, 100; KI, 0.5; CaCl$_2$.2H$_2$O, 150; CoCl$_2$.6H$_2$O, 100; H$_3$BO$_3$, 2.5; Na$_2$MoO$_4$.2H$_2$O, 0.25; KH$_2$PO$_4$, 50; EDTA, 3.724; FeSO$_4$.7H$_2$O, 2.784;

TABLE 2 mg/l: KNO$_3$, 500; Ca(NO$_3$)$_2$.3H$_2$O, 250; NH$_4$NO$_3$, 500; MgSO$_4$.7H$_2$O, 350; MnSO$_4$.H$_2$O, 25; CuSO$_4$.5H$_2$O, 0.05; ZnSO$_4$.7H$_2$O, 25; KI, 1; CaCl$_2$.2H$_2$O, 70; Cocl$_2$.6H$_2$O, 0.03; H$_3$BO$_3$, 5.5; Na$_2$MoO$_4$.2H$_2$O, 0.28; KH$_2$PO$_4$, 150; EDTA 40.9; FeSO$_4$.7H$_2$O, 30.

TABLE 3 mg/l: KNO$_3$, 100; H$_3$BO$_3$, 2.5; CaCl$_2$.2H$_2$O, 150; CuSO$_4$.5H$_2$O, 1; FeSO$_4$.7H$_2$O, 3; MgCl$_2$.6H$_2$O, 97.8; MgSO$_4$.7H$_2$O, 100; MnSO$_4$.H$_2$O, 2.5; KI, 0.5; KH$_2$PO$_4$, 5; NaMoO$_4$.2H$_2$O, 0.25; ZnSO$_4$.7H$_2$O, 2.

TABLE 4 mg/l: NH$_4$NO$_3$, 500; H$_3$BO$_3$, 5.5; CaCl$_2$.2H$_2$O, 70; Ca(NO$_3$)$_2$.4H$_2$O, 500; CoCl$_2$.6H$_2$O, 0.03; CuSO$_4$.5H$_2$O, 0.05; disodium EDTA, 40; FeSO$_4$.7H$_2$O, 30; MgSO$_4$.7H$_2$O, 350; MnSO$_4$.H$_2$O, 25; KI, 1; KNO$_3$, 500; KH$_2$PO$_4$, 150; NaMoO$_4$.2H$_2$O, 0.28; ZnSO$_4$.7H$_2$O, 25.

It should be noted that not every fruit from every variety or species of citrus will produce adventitious juice vesicles in vitro throughout the 120-210 age range; however, there will be an operative range within the 120-210 age period. To ascertain the operative age for a particular variety or species of citrus fruit, the following routine test is carried out. Juice vesicles from the test fruit are obtained at selected intervals within the 120-210 day range, e.g., 120, 130, 140, 150, 160, 170, 180, 190, 200, and 210 days. They are cultured as described above preferably using the medium of Table 2, and adventitious juice vesicle production is measured to ascertain which age range within the 120-210 range is operative.

The adventitious citrus juice vesicles of the invention have the unique characteristic that they branch out of pre-existing juice vesicles. This is in contrast to conventional tree-produced juice vesicles which arise out of the endocarp of the citrus fruit. Another feature of the adventitious citrus juice vesicles is that they are generally elliptical in shape.

It should be noted that although some varieties of pummelo and grapefruit have the ability to produce juice vesicles in vivo from pre-existing juice vesicles, these in vivo-produced pummelo and grapefruit vesicles differ from the adventitious juice vesicles of the invention in that they lack the ability to produce additional juice vesicles by branching from the surface of the vesicles. In contrast, the adventitious citrus juice vesicles of the invention have the ability to produce additional adventitious citrus juice vesicles through branching. It should be noted that species of citrus such as lemon, lime, and orange do not produce juice vesicles in vivo from pre-existing juice vesicles.

It is understood that the foregoing detailed description is given merely by way of illustration and that modification and variations may be made therein without departing from the spirit and scope of the invention.

What is claimed is:

1. Adventitious citrus juice vesicles resembling normal juice vesicles in that they are generally elliptical in shape, said vesicles having the following characteristics: they branch out of pre-existing intact citrus juice vesicles and they have the ability to produce additional adventitious citrus juice vesicles through branching.

2. Adventitious citrus juice vesicles from lemon, lime, or orange fruit, said vesicles having the characteristic that they branch out of pre-existing lemon, lime, or orange juice vesicles.

3. Adventitious juice vesicles as described in claim 2 having the additional characteristic that they have the ability to produce additional adventitious juice vesicles through branching.

4. Adventitious juice vesicles as described in claim 3 having the additional characteristic that they are generally elliptical in shape.

5. Adventitious citrus juice vesicles as described in claim 1 wherein said juice vesicles are pummelo or grapefruit juice vesicles.

* * * * *